(12) United States Patent
Tran (10) Patent No.: US 11,951,169 B2
(45) Date of Patent: Apr. 9, 2024

(54) PHARMACEUTICAL PREPARATION WITH CURCUMINOIDS NANOPARTICLES AND A METHOD FOR PRODUCING THE SAME

(71) Applicant: AASTAR PTE LTD, Singapore (SG)

(72) Inventor: The Huy Tran, Singapore (SG)

(73) Assignee: AASTAR PTE LTD., Singapore (SG)

( * ) Notice: Subject to any disclaimer, the term of this patent is extended or adjusted under 35 U.S.C. 154(b) by 280 days.

(21) Appl. No.: 17/422,735

(22) PCT Filed: Jan. 8, 2020

(86) PCT No.: PCT/SG2020/050007
§ 371 (c)(1),
(2) Date: Jul. 13, 2021

(87) PCT Pub. No.: WO2021/021014
PCT Pub. Date: Feb. 4, 2021

(65) Prior Publication Data
US 2022/0125931 A1     Apr. 28, 2022

(30) Foreign Application Priority Data
Jul. 26, 2019  (SG) ............ 10201906913Y (51) Int. Cl.
*A61K 47/44* (2017.01)
*A61K 9/48* (2006.01)
*A61K 31/12* (2006.01)

(52) U.S. Cl.
CPC ............ *A61K 47/44* (2013.01); *A61K 9/4875* (2013.01); *A61K 31/12* (2013.01)

(58) Field of Classification Search
CPC ...... A61K 47/44; A61K 9/4875; A61K 31/12; A61K 9/4858; A61K 9/4866; A61K 36/9066; A61K 47/22; A61K 47/26; A61K 9/1075; A61K 47/10; A61K 47/34; A61K 2300/00
See application file for complete search history.

(56) References Cited

U.S. PATENT DOCUMENTS

| 5,861,415 A | 1/1999 | Majeed et al. |
|---|---|---|
| 2012/0010297 A1 | 1/2012 | Chaniyilparampu et al. |
| 2014/0010903 A1 | 1/2014 | Madhavamenon et al. |
| 2018/0360774 A1 * | 12/2018 | Cavaleri .............. A61K 9/4866 |

FOREIGN PATENT DOCUMENTS

| WO | WO-2010010431 A1 * | 1/2010 | .......... A61K 31/121 |
|---|---|---|---|
| WO | 2014-031504 A1 | 2/2014 | |
| WO | 2017-195220 A1 | 11/2017 | |

* cited by examiner

*Primary Examiner* — Robert A Wax
*Assistant Examiner* — Quanglong N Truong
(74) *Attorney, Agent, or Firm* — Sinorica International Patent & Trademark (57) ABSTRACT

The present disclosure relates to a pharmaceutical composition having a mixture containing curcuminoids as at least one of the active therapeutic agents. Generally, the mixture comprises 4-8% by weight of purified curcuminoids; 20-35% by weight of an oil phase; 25-35% by weight of a co-solvent; and 40-50% by weight of a surfactant. Preferably, the purified curcuminoids in the mixture has an average size of about 19 nm or at least half of the curcuminoids carried in the mixture has particle size not exceeding 19 nm.

12 Claims, 6 Drawing Sheets

| Full Name/Short Name | Structure | Purity |
|---|---|---|
| Curcumin<br>(Curcumin I)<br>CUR | | >=98% |
| Demethoxycurcumin<br>(Curcumin II)<br>DMC | | >=98% |
| Bisdemethoxycurcumin<br>(Curcumin III)<br>BDMC | | >=98% |

PHARMACEUTICAL PREPARATION WITH CURCUMINOIDS NANOPARTICLES AND A METHOD FOR PRODUCING THE SAME

TECHNICAL FIELD

The present disclosure relates to a pharmaceutical composition having curcuminoids as an active therapeutic agent which shows improved bioavailability upon ingestion. More particularly, the curcuminoids particles suspended in the composition are prepared in nanosized to enhance their absorbability and thus bioavailability in a human subject taking the disclosed composition. Moreover, the present disclosure also provides a method for producing or manufacturing of the disclosed composition carrying nanosized curcuminoids.

BACKGROUND

Curcuminoids are polyphenolic compounds rendering the yellowish color of the Turmeric plants. Curcuminoids generally include curcumin (curcumin I), dimethoxy curcumin (curcumin II), bis-demethoxycurcumin (curcumin III) playing an important role in the Turmeric plants as the bioactive agents. These curcuminoids have been known to possess beneficial therapeutic effect towards some human diseases. Particularly, curcuminoids are reported being applicable as anti-inflammatory, anti-oxidant, anti-tumor, etc. In some researches, curcuminoids also show effective against Alzheimer's disease and gastrointestinal related disorders. For example, U.S. Pat. No. 5,861,415 describes method for isolating curcuminoids and using the isolated curcuminoids as bioprotectant to prevent free radicals in damaging the tissues. The purified curcuminoids are acquired by way of crystallization in the preparation of the disclosed bioprotectant. U.S. Pat. No. 9,192,644 discloses a curcuminoids formulation with enhanced bioavailability for treating Alzheimer's disease and other age-related disorders. The formulation disclosed includes an antioxidant in sufficient amount to avoid curcuminoids hydrolysis in addition to a water-solubilizing carrier. Optionally, the formulation can contain a glucuronidation inhibitor. Other usage of curcuminoids such as natural coloring agent can be found in U.S. patent application Ser. No. 09/935,684.

Despite curcuminoids excellent therapeutic effect, their real-life implementations as medicines and/or healthcare supplements have been greatly hampered by their poor water solubility hence bioavailability in human subjects. In view of that, much effort has been put into researches looking for ways to enhance curcuminoids water solubility. The enhancements generally focus on coupling curcuminoids to a suitable carrier or delivery system, modifying curcuminoid compounds chemically or reducing the size of the curcuminoids in a given pharmaceutical formulation. For instance, Bansal et al. claims another curcuminoids composition capable of self-emulsifying giving rise to curcuminoids nanoparticles with size below 200 nm International patent application no. PCT/IB2009/005154. The composition of this international patent application utilizes a lipid carrier system having hydrophilic-lipophilic balance in the range of 3 to 14 to deliver the desired composition. Likewise, Setthacheewakul et al. offers another self-emulsifying formulation of curcuminoids in their research publication which claims the curcuminoids particles in the liquid and pellet form of the formulation may respectively reach within the size of 25.8-28.8 nm and 29.6-32.8 nm. Further research published by Yan et al. describes another self-emulsifying drug delivery system for curcumin particles which have been reported to have particle size around 143 nm. Similar effort can be seen in publication of Y. Feng and J. Shao pertaining to a liquid self-emulsifying drug delivery system for curcumins using a mixture of emulsifiers having Capmul PG-8NF and Captex 200P in a weight ratio of 1:1. It is important to note that most of pharmaceutical compositions relating to curcuminoids disclosed in the abovementioned prior arts appears to have room for more improvements especially by way of reducing the curcuminoids particles size further to increase it solubility in the drug delivery system and bioavailability.

SUMMARY

The present disclosure aims to provide a pharmaceutical composition containing at least one active agent composed of curcuminoids or a mixture of curcumins. The disclosed composition exhibits great bioavailability for the curcuminoids thus bringing forth better therapeutic effects towards a human subject.

Further object of the present disclosure is directed to offer a pharmaceutical composition having curcuminoids nanoparticles in the size of 18 to 20 nm. Preferably, at least half of the curcuminoids suspended in the disclosed composition are in the size not exceeding 19 nm. The critically low particle size of the curcuminoids prepared in the disclosed composition permits better solubility and bioavailability upon ingestion by a human subject.

More object of the present disclosure relating to a pharmaceutical composition in which the active agents, curcuminoids as nanoparticles, are stable even being exposed to highly acidic environment.

Another object of the present disclosure pertains to a method for preparing a pharmaceutical composition comprising nanoparticles of curcuminoids or a mixture of different curcumins as a therapeutic active agent. The pharmaceutical composition acquired from the disclosed method possesses great solubility and bioavailability due to the relatively low particle size, about 19 nm, of the curcuminoids.

Further object of the disclosed method aims to employ relatively low toxicity solvents for extraction of curcuminoids from turmeric plants and purification of the extracted curcuminoids compared to prior arts.

At least one of the preceding objects is met, in whole or in part, by the present disclosure, in which one of the embodiments is associated with a pharmaceutical composition having a mixture comprising 0.5-10% by weight of purified curcuminoids; 1-35% by weight of an oil phase; 20-35% by weight of a co-solvent; and 20-80% by weight of a surfactant, wherein the purified curcuminoids are acquired by reacting crude curcuminoids with paraffin and iso-propanol. More particularly, the purified curcuminoids are acquired by dissolving a polar extract of turmeric powder with a solvent mixture comprising paraffin and iso-propanol followed by filtration to generate a filtrate and crystallization of the filtrate to produce crystal having the purified curcuminoids then drying the crystal to obtain standardization 95% purified curcuminoids.

For several embodiments, the purified curcuminoids in the mixture has an average size of about 19 nm. Alternatively, at least half of the particles or curcuminoids carried in the composition are in the size of not exceeding 19 nm.

For more embodiments, the pharmaceutical composition having a mixture comprising 0.5-10% by weight of purified curcuminoids; 1-35% by weight of an oil phase; 20-30% by weight of a co-solvent; and 20-80% by weight of a surfactant.

In some embodiments, the polar extract is acquired by extracting dried powder of turmeric with an organic polar extraction solvent using percolation extraction approach followed by separating the extraction solvent from the powder and concentrating the extraction solvent to produce the polar extract.

For several embodiments, the polar extract of turmeric powder is acquired by extracting dried turmeric powder with an alcohol using percolation extraction.

In more embodiments, the purified curcuminoids comprises curcumin I, curcumin II and curcumin III in a weight ratio of 80 to 85:10 to 15:1 to 5.

In some embodiments, the oil phase is any one or combination of soybean oil, castor oil, d-alpha tocopherol, and sunflower oil.

Likewise, the co-solvent is any one or combination of propylene glycol, polyethylene glycol 600, glycerin and sorbitol in several embodiments.

For a number of embodiments, the surfactant of the disclosed composition is any one or combination of Polyoxyl 40 Hydrogenate castor oil, Polyoxyl 35 Hydrogenate castor oil, polysorbate 80, and Poloxamer 407.

Another aspect of the present disclosure relates to a method of producing a pharmaceutical composition containing the curcuminoids nanoparticles. The method generally comprises the steps of providing dried pulverized powder of turmeric; reacting the powder with an organic polar extraction solvent using percolation extraction; acquiring a polar extract of the powder from the reacted extraction solvent; purifying the polar extract to obtain purified curcuminoids; mixing the purified curcuminoids with an oil phase, a co-solvent, and a surfactant in a weight ratio of 4-8:20-35:20-35:40-50 to produce the pharmaceutical composition. The purified curcuminoids in the produced pharmaceutical composition has an average size of about 19 nm.

In accordance to some embodiments of the disclosed method, the purifying step comprises dissolving the polar extract with a solvent mixture comprising paraffin and iso-propanol followed by filtration to generate a filtrate and crystallization of the filtrate to produce crystal having the purified curcuminoids then drying the crystal to obtain standardization 95% purified curcuminoids.

For further embodiments of the mentioned method, the polar extract is acquired byway of concentrating the reacted extraction solvent.

Still, for some embodiments, the organic polar extraction solvent is alcohol, ester or any combination derived thereof.

DETAILED DESCRIPTION

The present disclosure may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope Unless specified otherwise, the terms "comprising" and "comprise" as used herein, and grammatical variants thereof, are intended to represent "open" or "inclusive" language such that they include recited elements but also permit inclusion of additional, un-recited elements.

As used herein, the terms "approximately" or "about", in the context of concentrations of components, conditions, other measurement values, etc., means+/−5% of the stated value, or +/−4% of the stated value, or +/−3% of the stated value, or +/−2% of the stated value, or +/−1% of the stated value, or +/−0.5% of the stated value, or +/−0% of the stated value.

One aspect of the present disclosure refers to a pharmaceutical composition capable of offering therapeutic effect against one or more diseased state known in the field treatable by curcuminoids. As setting forth, the disclosed pharmaceutical composition can be prepared through a method rendering the curcuminoids carried or suspended in the composition being extremely low in particle size. The reduced particle size enhances solubility and bioavailability of curcuminoids upon ingestion by a human subject. In a number of embodiments, the composition has a mixture which generally comprises 4%-8% by weight of purified curcuminoids; 20-35% by weight of an oil phase; 25-35% by weight of a co-solvent; and 40%-50% by weight of a surfactant. Preferably, the purified curcuminoids in the mixture has an average size of about 19 nm. Alternatively, at least half of the curcuminoids in the composition is around 19-20 nm or below to acquire the excellent solubility and bioavailability.

In accordance with some preferred embodiments, the purified curcuminoids employed in the mentioned composition are acquired by purifying a polar extract of turmeric having crude curcuminoids with paraffin and iso-propanol such that the derived purified curcuminoids become ideal for subsequent preparation of the composition. The purification of the polar extract of turmeric is by way of crystallization of the polar extract, preferably in the form of concentrated powder, dissolved in paraffin and isopropanol to remove any undesired impurities. More specifically, the turmeric or the polar extract containing the crude curcuminoids is dissolved into a purifying solvent derived from mixing paraffin wax and iso-propanol. The polar extract is dissolved into paraffin wax and iso-propanol at a weight ratio of 10:1:4. To facilitate the dissolution of the turmeric extract, the mixture of the turmeric extract and the purifying solvent may be subjected to continuous stirring for 5 to 60 minutes. The mixture is then left for 3 to 24 hours for completing the dissolution including precipitation of undissolved particles before being subjected to a filtration process to acquire a filtrate. The acquired filtrate is subsequently conditioned for crystallization giving rise to crystals having the purified curcuminoids usable for the preparation of the mentioned pharmaceutical composition. The produced crystal is further dried at 70° C. to obtain standardization 95% purified curcuminoids. Furthermore, in some embodiments, the polar extract or turmeric extract having the crude curcuminoids utilized in the present disclosure is preferably acquired from extracting dried turmeric powder with an organic polar extraction solvent using percolation extraction approach followed by separating the extraction solvent from the extracted powder and concentrating the extraction solvent to finally yield the polar extract. Alcohol such as ethanol, ester like ethyl acetate or any combination thereof can be employed as the polar extraction solvent. For more embodiments, the dried turmeric powder can be processed from fresh turmeric root harvested from the field followed by drying the root to the desired humidity and pulverizing the dried root into the powder form facilitating the extraction efficiency through the percolation extraction. Preferably, the turmeric plant powder is in the size of 0.5 mm to 2 mm.

For a number of embodiments, the purified curcuminoids carried or suspended in the disclosed composition comprises curcumin I, curcumin II and curcumin III. More preferably, the curcumin I, curcumin II and curcumin III are in a weight ratio of 80 to 85:10 to 15:1 to 5 in order to cater the desired therapeutic benefits. It is important to note that the weight ratio of each curcuminoids in the composition may be modified accordingly to obtain the ideal therapeutic outcome.

Pursuant to several embodiments, the oil phase of the disclosed composition can be any one or combination of soybean oil, castor oil, d-alpha tocopherol, and sunflower oil. The oil phase facilitates suspending the curcuminoids active agent in the emulsion formed within the mixture of the composition. In more preferable embodiments, the oil phase is of natural origin particularly plant-based to better ensure safety about usage of the disclosed composition.

To work better with the oil phase in attaining the desired particle size, the surfactant used is any one or combination of Polyoxyl 40 Hydrogenate castor oil, Polyoxyl 35 Hydrogenate castor oil, polysorbate 80, and Poloxamer 407. The surfactant stabilizes the produced emulsion preserving the curcuminoids in the preferred particle of nano size thus prolonging the shelf life of the disclosed composition.

Similarly, the co-solvent is any one or combination of propylene glycol, polyethylene glycol 600, glycerin and sorbitol. For several embodiments, the co-solvent serves as an excipient capable of enhancing therapeutic effects of the curcuminoids and/or stabilizing the created emulsion of the curcuminoids.

Preferably, the disclosed composition is a gel liquid or gel capsule formulation.

Figure 1:
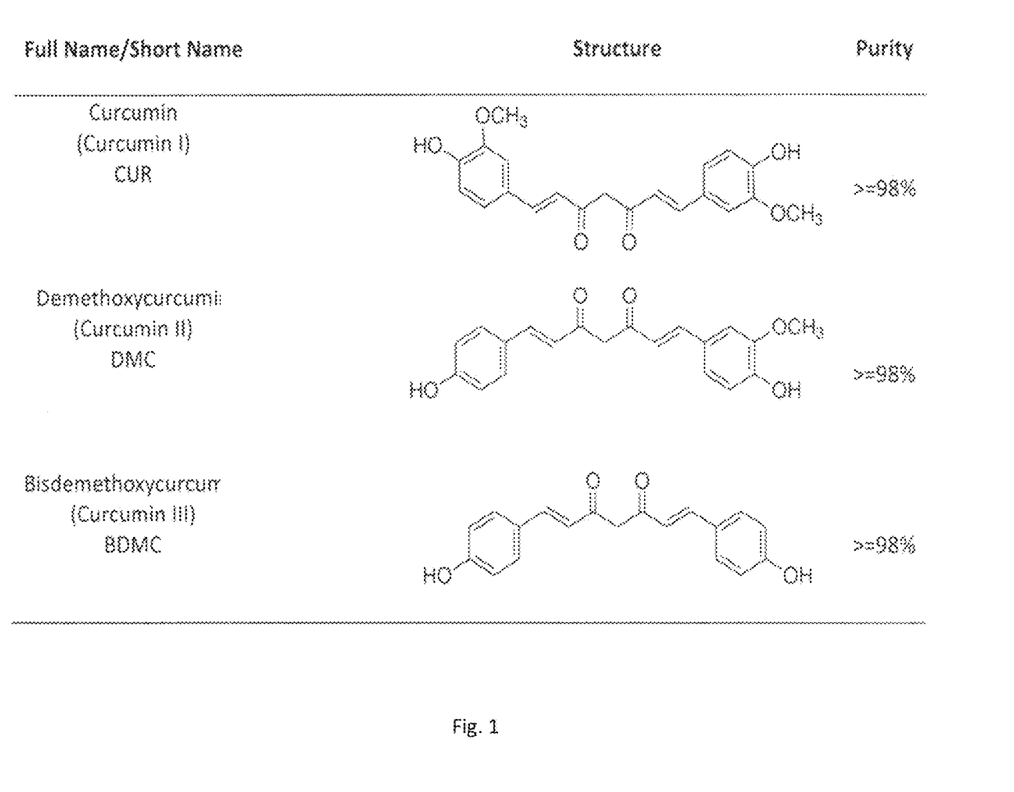
FIG. 1 shows chemical structures of different curcuminoids components carried in embodiments of the disclosed pharmaceutical composition.
Figure 2:
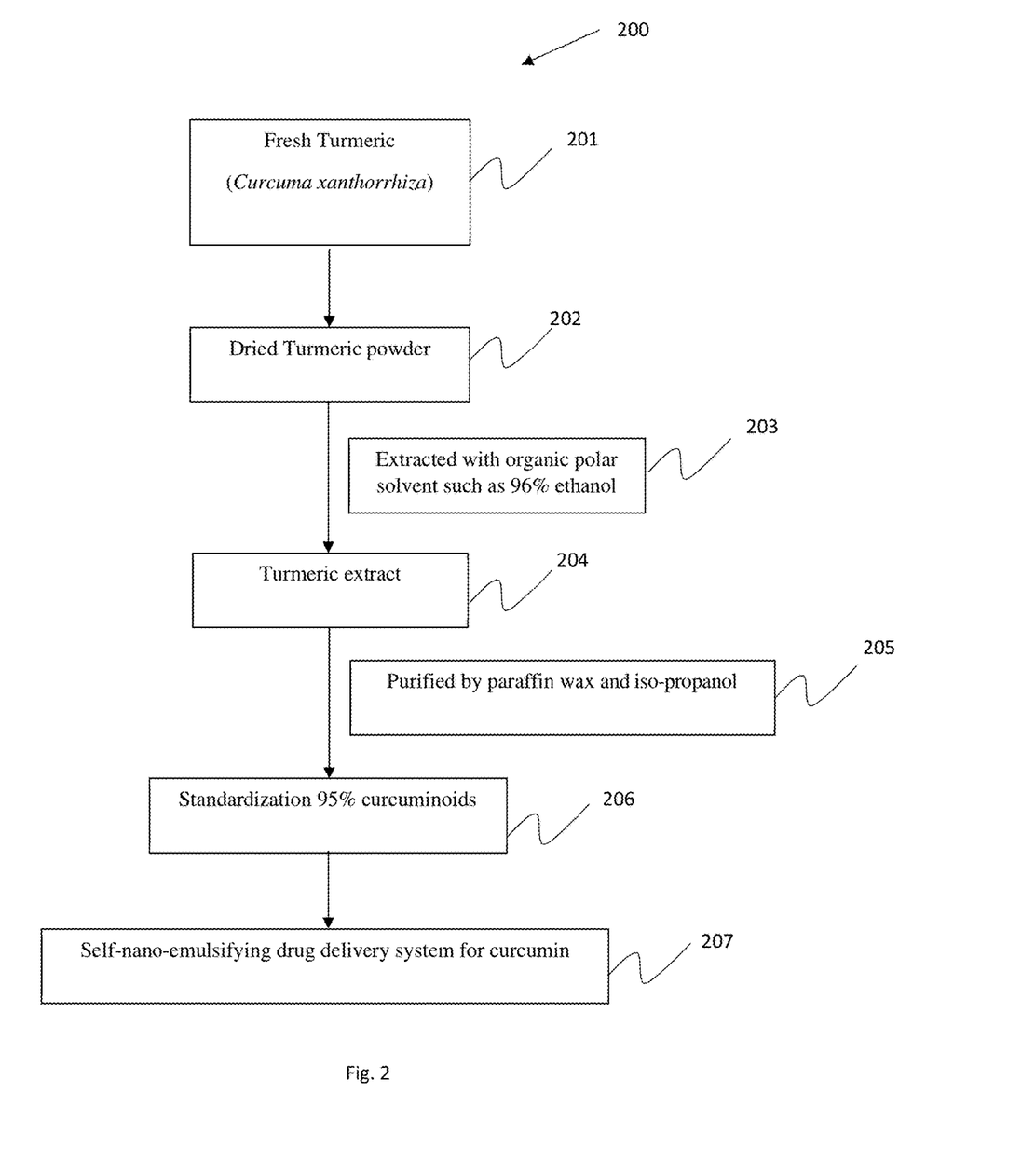
FIG. 2 is a flowchart depicting the steps can be taken in several embodiments of the disclosed method in preparing the pharmaceutical composition containing curcuminoids with the desired particles size for enhanced bioavailability.

Another aspect of the present is associated to a method 200 of producing a pharmaceutical composition containing at least curcuminoids as an active agent for initiating therapeutic effect in a human subject upon orally ingesting the composition.

The method 200 comprises providing dried pulverized powder of turmeric 202; reacting the powder of turmeric with an organic polar extraction solvent using percolation extraction to dissolve crude curcuminoids into the extraction solvent 203; acquiring a polar extract from the reacted extraction solvent 204; purifying the polar extract to obtain purified curcuminoids 205; and mixing the purified curcuminoids with an oil phase, a co-solvent, and a surfactant in a weight ratio of 4-8:20-35:25-35:40-50 to produce the pharmaceutical composition 207.

The purified curcuminoids in the produced pharmaceutical composition has an average size of about 19 nm.

In more details, the powder of turmeric can be harvested fresh turmeric plants like *Curcuma xanthorrhiza* 201. Preferably, the plant parts such as root abundant with curcuminoids are collected for subsequent processes to produce the desired composition. The collected plant parts are preferably washed with water to remove any dirt and contaminants. Also, in more embodiments, some damaged plant parts are filtered off from being proceeded to extraction of curcuminoids. The cleaned plant parts are then dried to reduce the water content and humidity to avoid any disruption towards the succeeding percolation extraction 202. The drying can be performed by way of heating through heater or sun. Drying via heater allows more control over the time and the final water content retained in the dried plant parts, while drying using the heat from sun is more cost-saving. The dried turmeric plant parts are preferably further reduced in size to favor the extraction of the crude curcuminoids. The dried plant parts are pulverized or ground in a diameter around 0.5 mm to 2 mm. Optionally, the powder of the dried turmeric plants may be subjected to sieving for selecting powder to predetermined size for the extraction such that the effect of the extraction towards the pulverized turmeric powder becomes more uniform throughout the extraction process.

In the extraction step 203 of the dried turmeric powder, hydrophilic and/or polar organic solvent like alcohol including ethanol, ester including ethyl acetate, or any combination derived thereof are brought into contact with the dried turmeric powder to extract crude curcuminoids from the matrix of the turmeric powder. According to a number of embodiments, the dried powder of turmeric can be extracted using ethanol 96% by percolation extraction method to dissolve the curcuminoids from the powder into the polar solvent used. The weight ratio of the polar extraction solvent to the turmeric powder is 3 to 5:1. The used polar extraction solvent is then separated from the powder of turmeric. In order to obtain a polar extract, the used extraction solvent is further subjected to vaporization to concentrate the curcuminoids dissolved in the used extraction solvent 204. The vaporization of the used extraction solvent can be carried out by way of heating and/or reduced air pressure. Once the used extraction solvent has been completely removed, the polar extract or turmeric extract or crude curcuminoids are ready for further purification. Literally, the polar extract is acquired by way of concentrating the reacted extraction solvent. Moreover, the organic polar extraction solvent is alcohol, ester or any combination derived thereof. Alcohol such as ethanol or ester like ethyl acetate can be used in the disclosed method for polar extraction of the turmeric powder.

In the purification stage 205, the polar extract or crude curcuminoids are reacted with paraffin wax and iso-propanol to obtain standardization 95% purified curcuminoids 206. More specifically, the turmeric or the polar extract containing the crude curcuminoids is dissolved into a purifying solvent derived from mixing paraffin wax and iso-propanol.

In more details, the turmeric extract is dissolved into paraffin wax and iso-propanol at a weight ratio of 10:1:4. To facilitate the dissolution of the turmeric extract, the mixture of the turmeric extract and the purifying solvent are subjected to continuous stirring for 5 to 60 minutes. The mixture is then left for 3 to 24 hours for completing the dissolution including precipitation of undissolved particles before being subjected to a filtration process to acquire a filtrate. The acquired filtrate is subsequently conditioned for crystallization giving rise to crystals having the purified curcuminoids usable for the preparation of the mentioned pharmaceutical composition. The produced crystal is further dried at 70° C. to obtain standardization 95% purified curcuminoids. In short, the purifying step comprises dissolving the polar extract with a solvent mixture comprising paraffin and iso-propanol followed by filtration to generate a filtrate and crystallization of the filtrate to produce crystal having the purified curcuminoids then drying the crystal to obtain standardization 95% purified curcuminoids.

In step 207, the purified curcuminoids is mixed with an oil phase, a co-solvent, and a surfactant in a weight ratio of 4-8:20-35:25-35:40-50 to produce the pharmaceutical composition. As mentioned in the foregoing description, the purified curcuminoids in the mixture of the obtained composition has an average size of about 19 nm. Alternatively, at least half of the curcuminoids in the composition is around 19-20 nm or below to acquire the excellent solubility and bioavailability.

In accordance with several embodiments, the oil phase applicable for the abovementioned method is any one or combination of soybean oil, castor oil, d-alpha tocopherol, and sunflower oil. Preferably, the oil phase used in some of the embodiments of the disclosed method are of natural origin to minimize any potential toxicity caused by the like counterparts synthesized chemically. Similarly, the co-solvent is any one or combination of propylene glycol, polyethylene glycol 600, glycerin and sorbitol. Also, the surfactant is any one or combination of Polyoxyl 40 Hydrogenate castor oil, Polyoxyl 35 Hydrogenate castor oil, polysorbate 80, and Poloxamer 407. Preferably, the purified curcuminoids suspended in the produced composition comprises curcumin I, curcumin II and curcumin III in a ratio of 80% to 85%:10% to 15%:1% to 5%.

Example 1

The density and pH (diluted 1:50 with distilled water) of the gel liquid were measured using a density bottle and a pH meter respectively. The size of the curcuminoids in the gel liquid was measured using a Zetasizer machine (Malvern Instruments).

Density and the pH values measured is shown in the Table 1 below, while the particle size detected using Zetasizer machine is provided in Table 2.

TABLE 1

Density and pH of Nano Gel Liquid
Physical Characteristics

| Density | 1.0451 g/ml |
|---|---|
| pH | 4.90 |

TABLE 2

Particle Size Determination of Nano Gel Liquid
Nano-Particle Size

| Size | 18.905 nm |
|---|---|

Example 2

Figure 3:
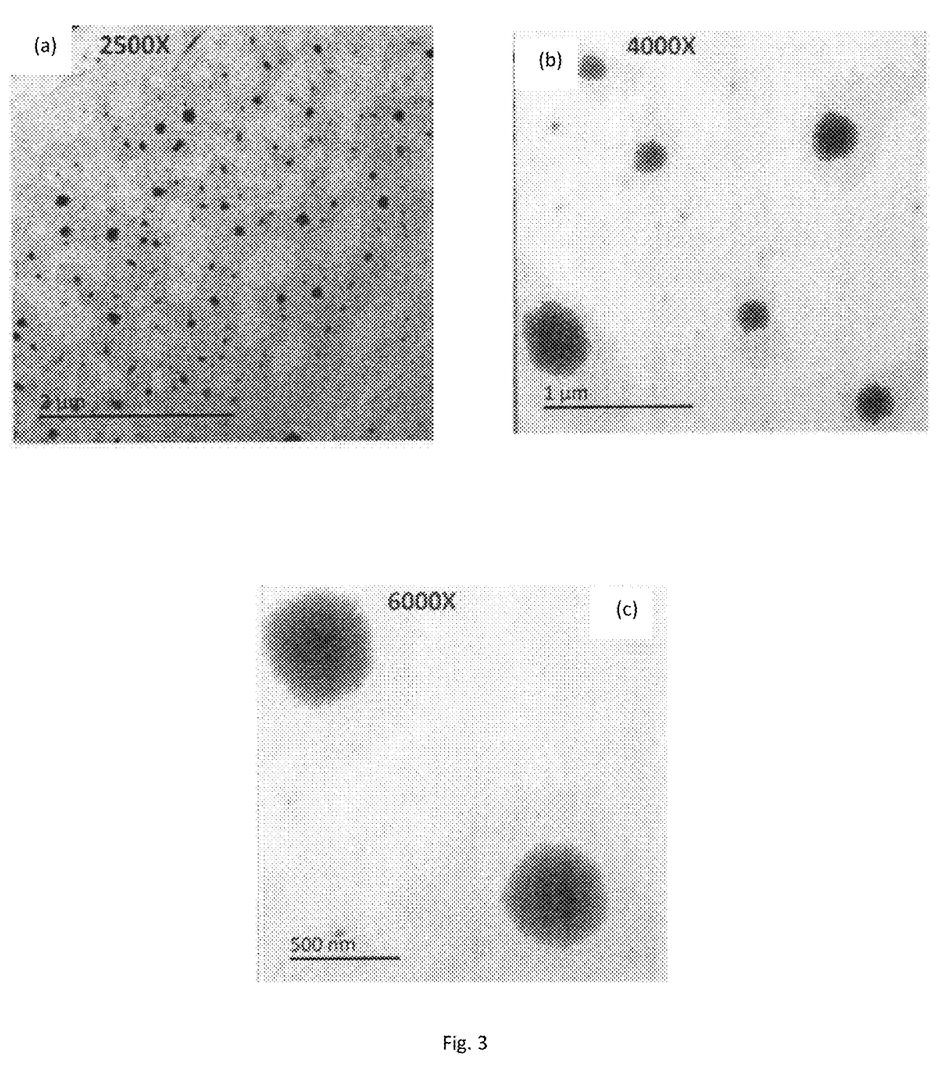
FIG. 3 shows images of transmission electron microscopy at various magnifications where (a) is at 2500×, (b) is at 4000× and (c) is at 6000×.
Figure 4:
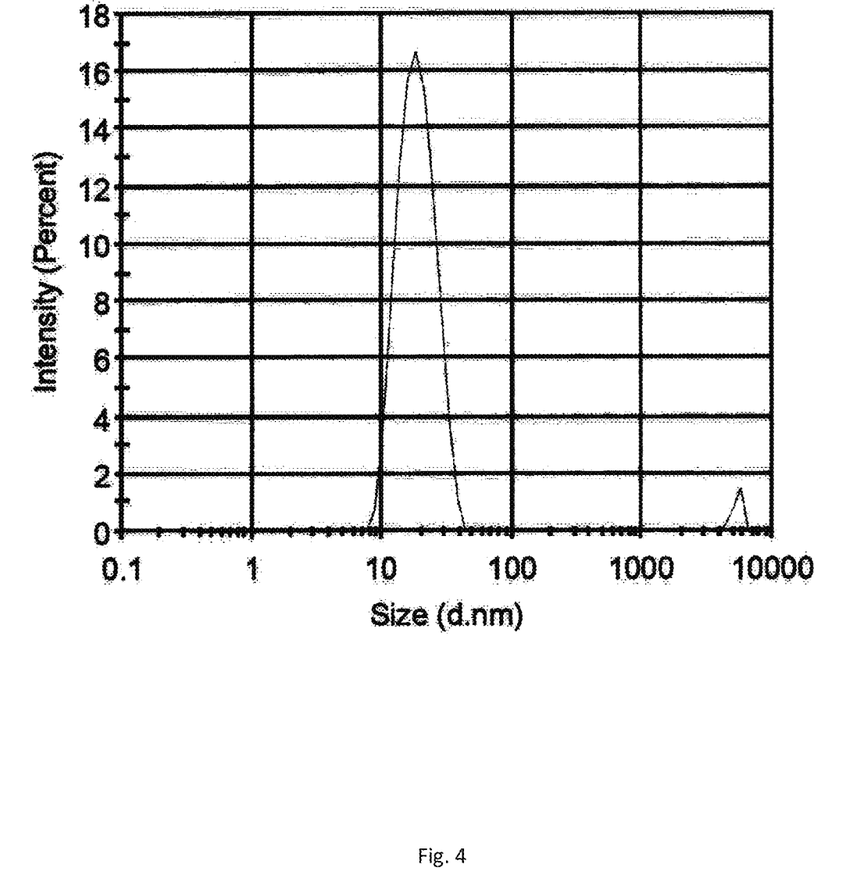
FIG. 4 is a graph showing distribution of the particles size in one embodiment of the disclosed composition.
Figure 5A:
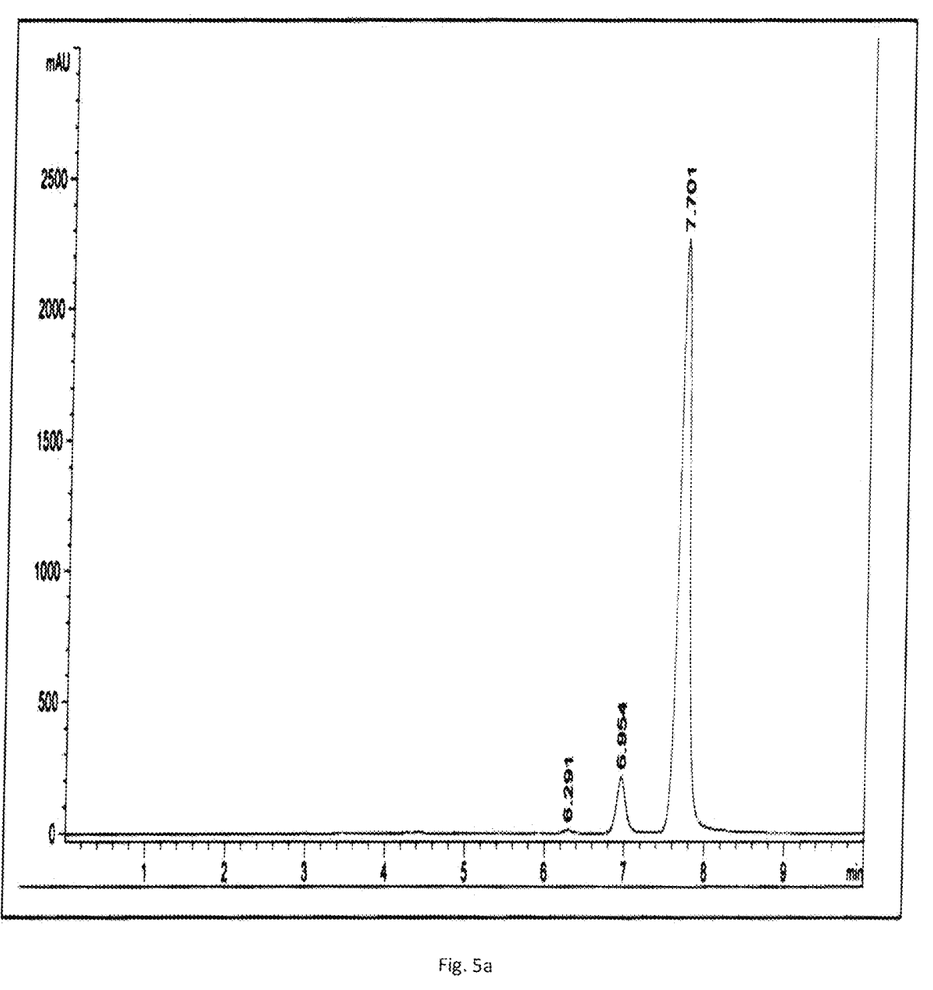
FIG. 5(a) is a HPLC chromatogram for analysis on the embodiment of the composition referred in FIG. 4.
Figure 5B:
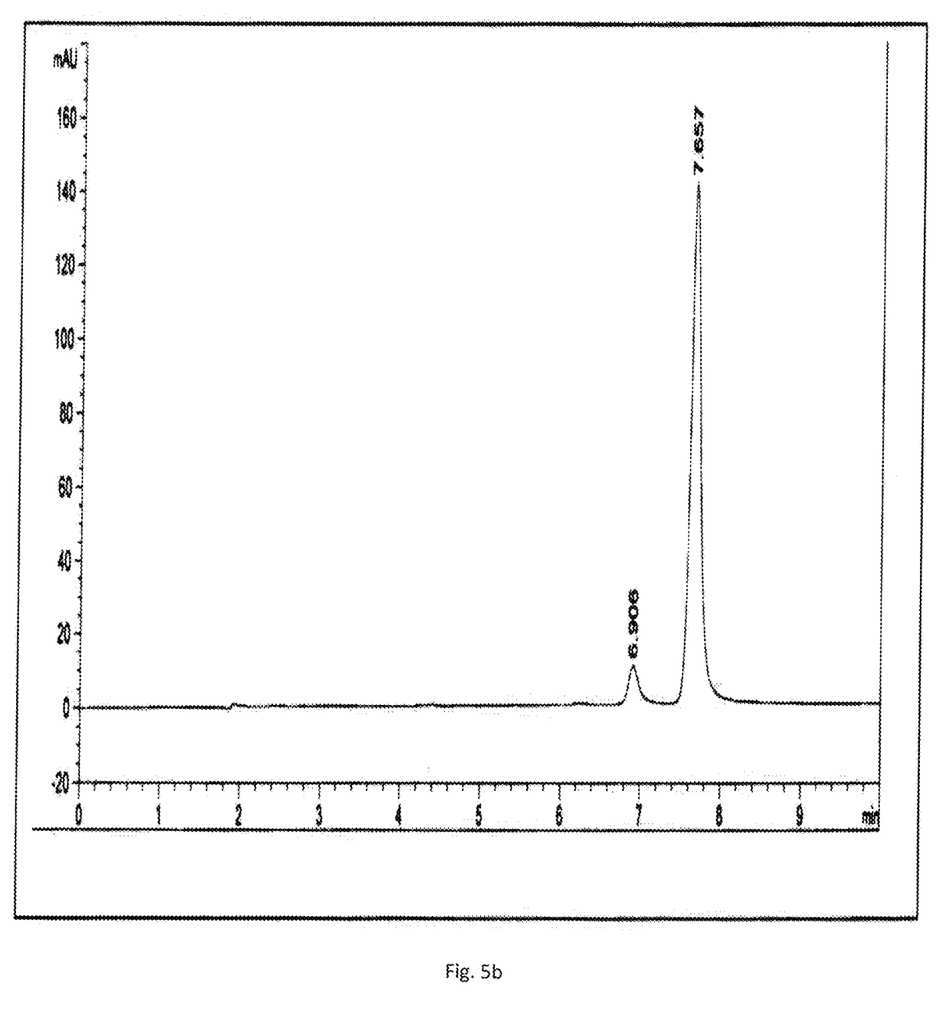
FIG. 5(b) is a HPLC chromatogram for analysis on the dissolution sample described in Example 4

A transmission Electron Microscope (model JEOL JEM-1230) was used to photograph the structure of the gel liquid diluted 1:500 in distilled water. Samples were first vortexed for 1 minute and a drop of the diluted solution was placed on a carbon-coated copper grid (300 mesh), allowed to stand at room temperature for 10 minutes, before the excess liquid was blotted with a filter paper and air dried for 5 minutes. The sample was then negatively stained with 2% phosphotungstic acid (PTA) for 2 minutes and excess PTA was removed. The grid was subsequently examined under TEM at an acceleration voltage of 120 kV and being photographed at the magnifications of (a) 2500×, (b) 4000× and (c) 6000×. The images taken are illustrated in FIG. 3

Example 3

1.7 mg of curcumin (CUR), 1.1 mg of demthoxycurcumin (DMC) and 1.2 mg of bis demthoxycurcumin (BDMC) were accurately weighted and dissolved into HPLC grade methanol to yield 0.63 mg/ml, 1 mg/ml and 1 mg/ml, respectively, to obtain stock solutions. A mixed series of dilutions with methanol form the stock solution was performed subsequently.

0.4 g of the disclosed gel liquid from a capsule of one disclosed composition was squeezed into a 50 ml centrifuge tube, followed by adding 40 ml of ultrapure water to completely dissolve the gel liquid forming a sample solution. Two ml of the sample solution dissolved with the gel liquid was then filtered through a 0.45 μm membrane into a HPLC vial for CUR analysis. A 5-fold dilution of the sample solution was performed for CUR HPLC analysis. 2 ml of the diluted solution was filtered through a 0.45 μm membrane into a HPLC vial for CUR analysis. The results acquired is provided in Table 3 below.

TABLE 3

| | Nano gel capsule | | Nano gel liquid | |
|---|---|---|---|---|
| | Content (% w/w) | RSD (%) | Content (% w/w) | RSD (%) |
| CUR (curcumin I) | 4.792 ± 0.15708 | 3.28 | 5.084 ± 0.0201 | 1.25 |
| DMC (curcumin II) | 0.241 ± 0.00305 | 1.26 | 0.252 ± 0.0037 | 1.49 |
| BDMC (curcumin III) | 0.009 ± 0.00013 | 1.38 | 0.01 ± 0.00013 | 0.40 |

Example 4

An Agilent 1260 Infinity HPLC system consists of a G1330B thermostat, a G1329B auto-injector, a G13150 diode array detector, a G1322A degasser and a high-pressure binary pump. Signal/Noise ratio of the chromatogram generated from this HPLC was used for qualitative and quantitative analyses in this study. The column used was an Angilent Poroshell 120 EC-C18 (3.0×1150 mm, 2.7 am). The HPLC was run for 10 minutes at a column temperature of 35° C. under a flow rate of 0.3 ml/min with injection volume being 5 μl. The detection spectrum was set at 426 nm using an elusion medium comprising acetonitrile and 0.1% of aqueous formic acid in a volume ratio of 1:2.

2.0 g of NaCl and 7 ml of HCl were dissolved in 1 L of ultrapure water. The pH was adjusted to 1.2, by using 2M NaOH. 13.121 g of $Na_2HPO_4$ were dissolved in 1 L of ultrapure water. The pH was adjusted to 6.8.

A Vankel Varain VK 70000 Dissolution System consisting of VK7000 dissolution system, VK 750D heating circulator, system monitor, 6 Vankel vessels and apparatus Type II paddles, was used in the preparation of a dissolution sample from capsules containing the gel liquid.

The dissolution test was performed in compliance with United States Pharmacopoeia using apparatus Type II paddles. 500 ml of pH 1.2 HCl solution was added into the dissolution vessel. 6 capsules were added into 6 vessels respectively. 1-2 ml of the dissolution sample were collected at 10 minutes, 15 minutes and 45 minutes using 3 ml syringe and filtered immediately using a 0.45 μm membrane into a HPLC vial. 2 μl of the filtrate was injected into the HPLC system for analysis.

Further, 250 ml of pH 6.8 solution was added to the same vessel at 45 minutes and the pH was adjusted to 6.8 using 2M NaOH within 5 minutes. 1-2 ml of the dissolution sample was then collected after 60 minutes, 75 minutes and 120 minutes followed by filtering through a 0.45 µm membrane immediately. 2 µl of the filtrate was injected into the HPLC system for analysis. The results of the dissolution test can be found in Table 4 below.

TABLE 4

|  |  | Curcumin (curcumin I) | | DMC (curcumin II) | | BDMC (curcumin III) | |
| --- | --- | --- | --- | --- | --- | --- | --- |
|  |  | Weight (µg) | RSD | Weight (µg) | RSD | Weight (µg) | RSD |
| pH 1.2 | 10 min | 590 ± 78 | 13% | ND | ND | ND | ND |
|  | 15 min | 4250 ± 686 | 16% | 195 ± 22 | 11% | ND | ND |
|  | 30 min | 18908 ± 1819 | 9% | 831 ± 87 | 11% | ND | ND |
| pH 6.8 | 45 min | 24155 ± 1397 | 6% | 745 ± 48 | 6% | ND | ND |
|  | 60 min | 23746 ± 1347 | 6% | 747 ± 45 | 6% | ND | ND |
|  | 75 min | 23497 ± 1859 | 8% | 739 ± 68 | 9% | ND | ND |
|  | 120 min | 23937 ± 1826 | 8% | 763 ± 69 | 9% | ND | ND |

ND: Not detected

It is to be understood that the present invention may be embodied in other specific forms and is not limited to the sole embodiment described above. However, modification and equivalents of the disclosed concepts such as those which readily occur to one skilled in the art are intended to be included within the scope of the claims which are appended thereto

The invention claimed is:

1. A pharmaceutical composition having a mixture comprising:
    4-8% by weight of purified curcuminoids;
    20-35% by weight of an oil phase;
    25-35% by weight of a co-solvent; and
    40-50% by weight of a surfactant,
    wherein the purified curcuminoids are acquired by dissolving a polar extract of turmeric powder with a solvent mixture comprising paraffin and iso-propanol followed by filtration to generate a filtrate and crystallization of the filtrate to produce crystal having the purified curcuminoids then drying the crystal to obtain standardization 95% purified curcuminoids,
    wherein the purified curcuminoids in the mixture has an average size of about 19 nm,
    wherein the purified curcuminoids comprises curcumin I, curcumin II and curcumin III in a weight ratio of 80 to 85:10 to 15:1 to 5.

2. The pharmaceutical composition of claim 1, wherein the polar extract is acquired by extracting dried powder of turmeric with an organic polar extraction solvent using percolation extraction approach followed by separating the extraction solvent from the powder and concentrating the extraction solvent to produce the polar extract.

3. The pharmaceutical composition of claim 1, wherein the oil phase is any one or combination of soybean oil, castor oil, d-alpha tocopherol, and sunflower oil.

4. The pharmaceutical composition of claim 1, wherein the co-solvent is any one or combination of propylene glycol, polyethylene glycol 600, glycerin and sorbitol.

5. The pharmaceutical composition of claim 1, wherein the surfactant is any one or combination of Polyoxyl 40 Hydrogenate castor oil, Polyoxyl 35 Hydrogenate castor oil, polysorbate 80, and Poloxamer 407.

6. The pharmaceutical preparation of claim 1 is a gel liquid or gel capsule formulation.

7. The pharmaceutical preparation of claim 2, wherein the organic polar extraction solvent is alcohol, ester or any combination derived thereof.

8. A method of producing a pharmaceutical composition comprising:
    providing dried pulverized powder of turmeric;
    reacting the powder with an organic polar extraction solvent using percolation extraction;
    acquiring a polar extract of the powder from the reacted extraction solvent;
    purifying the polar extract to obtain purified curcuminoids;
    mixing the purified curcuminoids with an oil phase, a co-solvent, and a surfactant in a weight ratio of 4-8:20-35:20-35:40-50 to produce the pharmaceutical composition, wherein the purified curcuminoids in the produced pharmaceutical composition has an average size of about 19 nm, wherein the purifying comprises dissolving the polar extract with a solvent mixture comprising paraffin and iso-propanol followed by filtration to generate a filtrate and crystallization of the filtrate to produce crystal having the purified curcuminoids then drying the crystal to obtain standardization 95% purified curcuminoids, wherein the purified curcuminoids comprises curcumin I, curcumin II and curcumin III in a weight ratio of 80 to 85:10 to 15:1 to 5.

9. The method of claim 8, wherein the polar extract is acquired by way of concentrating the reacted extraction solvent.

10. The method of claim 8, the oil phase is any one or combination of soybean oil, castor oil, d-alpha tocopherol, and sunflower oil.

11. The method of claim 8, wherein the co-solvent is any one or combination of Propylene Glycol, polyethylene glycol 600, glycerin and sorbitol.

12. The method of claim 8, wherein the surfactant is any one or combination of Polyoxyl 40 Hydrogenate castor oil, Polyoxyl 35 Hydrogenate castor oil, polysorbate 80, and Poloxamer 407.

* * * * *